(12) United States Patent
Zakzeski et al.

(10) Patent No.: US 9,714,227 B2
(45) Date of Patent: Jul. 25, 2017

(54) CATALYST FOR THE EPOXIDATION OF ALKENES

(71) Applicant: BASF SE, Ludwigshafen (DE)

(72) Inventors: Joseph J. Zakzeski, Ludwigshafen (DE); Marco Bosch, Lampertheim (DE); Cornelia Dobner, Ludwigshafen (DE); Christian Bartosch, Mannheim (DE); Jürgen Zühlke, Speyer (DE)

(73) Assignee: BASF SE

( * ) Notice: Subject to any disclaimer, the term of this patent is extended or adjusted under 35 U.S.C. 154(b) by 0 days.

(21) Appl. No.: 15/102,654

(22) PCT Filed: Dec. 1, 2014

(86) PCT No.: PCT/IB2014/066466
§ 371 (c)(1),
(2) Date: Jun. 8, 2016

(87) PCT Pub. No.: WO2015/087194
PCT Pub. Date: Jun. 18, 2015

(65) Prior Publication Data
US 2016/0297781 A1    Oct. 13, 2016

(30) Foreign Application Priority Data
Dec. 9, 2013  (EP) .................... 13196259

(51) Int. Cl.
| | | |
|---|---|---|
| B01J 27/02 | (2006.01) | |
| B01J 27/055 | (2006.01) | |
| B01J 27/047 | (2006.01) | |
| C07D 301/03 | (2006.01) | |
| C07D 301/10 | (2006.01) | |
| B01J 23/68 | (2006.01) | |
| B01J 35/10 | (2006.01) | |
| B01J 21/04 | (2006.01) | |
| B01J 37/08 | (2006.01) | |
| B01J 35/00 | (2006.01) | |
| B01J 35/02 | (2006.01) | |
| B01J 37/02 | (2006.01) | |

(52) U.S. Cl.
CPC ........... *C07D 301/10* (2013.01); *B01J 21/04* (2013.01); *B01J 23/688* (2013.01); *B01J 27/047* (2013.01); *B01J 35/0006* (2013.01); *B01J 35/109* (2013.01); *B01J 35/1009* (2013.01); *B01J 35/1066* (2013.01); *B01J 35/1071* (2013.01); *B01J 35/1076* (2013.01); *B01J 37/0215* (2013.01); *B01J 37/0236* (2013.01); *B01J 37/088* (2013.01); *B01J 27/055* (2013.01); *B01J 35/002* (2013.01); *B01J 35/026* (2013.01); *B01J 35/1038* (2013.01); *B01J 37/0213* (2013.01); *B01J 2523/00* (2013.01); *Y02P 20/52* (2015.11)

(58) Field of Classification Search
CPC ............... C07D 301/10; B01J 35/1071; B01J 35/1009; B01J 35/1076; B01J 35/0006; B01J 35/1016; B01J 35/109; B01J 37/0215; B01J 37/0236; B01J 37/088; B01J 27/047; B01J 21/04

USPC .......................... 549/536; 502/216, 218, 219
See application file for complete search history.

(56) References Cited

U.S. PATENT DOCUMENTS

| | | | |
|---|---|---|---|
| 4,007,135 A | 2/1977 | Hayden et al. | |
| 4,324,699 A | 4/1982 | Mross et al. | |
| 4,389,338 A | 6/1983 | Mitsuhata et al. | |
| 4,732,918 A | 3/1988 | Lohmueller et al. | |
| 4,774,222 A | 9/1988 | Rashkin | |
| 5,011,809 A | 4/1991 | Herzog et al. | |
| 2005/0096219 A1 | 5/2005 | Szymanski et al. | |
| 2009/0062556 A1* | 3/2009 | Pak ........................ | B01J 23/50 549/534 |
| 2009/0198076 A1 | 8/2009 | Guckel | |
| 2009/0270640 A1 | 10/2009 | Maurer et al. | |
| 2012/0264951 A1 | 10/2012 | Rosendahl et al. | |
| 2012/0323026 A1* | 12/2012 | Lockemeyer ......... | B01J 27/051 549/536 |
| 2013/0109871 A1 | 5/2013 | Rosendahl et al. | |

FOREIGN PATENT DOCUMENTS

| | | |
|---|---|---|
| CA | 1026763 A | 2/1978 |
| DE | 23 00 512 A1 | 7/1973 |
| DE | 24 54 972 A1 | 6/1975 |
| DE | 25 21 906 A1 | 12/1975 |
| DE | 27 53 359 A1 | 6/1979 |
| DE | 31 50 205 A1 | 8/1982 |
| DE | 33 21 895 A1 | 12/1983 |

(Continued)

OTHER PUBLICATIONS

International Search Report for PCT/IB2014/066466 mailed Apr. 1, 2015.
Prasad, S., Thiotungstate isopolyanions: and electrometric study, J.Chem., 1981, vol. 59, pp. 563-565.
Singh Gaur, R.P., "Modern Hydrometallurigical Production Methods for Tungsten", JOM, 2006, vol. 58, Issue 9, pp. 45-49.
Ultmanns Encyclopedia of Industrial Chemistry, 1987, vol. A-10, pp. 117-135.
International Preliminary Examination Report on Patentability for PCT/IB2014/066466 (PCT counterpart to this application) mailed Jun. 14, 2016.
Extended European Search Report for EP Patent Application No. 14869091.0, Issued on May 2, 2017, 7 pages.

*Primary Examiner* — T. Victor Oh
(74) *Attorney, Agent, or Firm* — Drinker Biddle & Reath LLP

(57) ABSTRACT

The present invention relates to a catalyst for the epoxidation of alkenes, comprising silver, rhenium, cesium, lithium, tungsten and sulfur on a support. The present invention further relates to a process for producing the catalyst and the use of the catalyst for the oxidation of alkylenes to alkylene oxides. In addition, the present invention relates to a process for preparing ethylene oxide from ethylene, which comprises the oxidation of ethylene with oxygen in the presence of said catalyst.

19 Claims, No Drawings

(56) References Cited

FOREIGN PATENT DOCUMENTS

| | | |
|---|---|---|
| DE | 34 14 717 A1 | 10/1985 |
| DE | 25 60 684 C2 | 10/1989 |
| EP | 0011356 A1 | 5/1980 |
| EP | 14 457 A2 | 8/1980 |
| EP | 0082609 A1 | 6/1983 |
| EP | 0085237 A1 | 8/1983 |
| EP | 0172565 A2 | 2/1986 |
| EP | 0229465 A1 | 7/1987 |
| EP | 0266015 A1 | 5/1988 |
| EP | 0339748 A2 | 11/1989 |
| EP | 0357293 A1 | 3/1990 |
| EP | 384 312 A1 | 8/1990 |
| EP | 0 480 538 A1 | 4/1992 |
| EP | 0496386 A1 | 7/1992 |
| EP | 1613428 A2 | 1/2006 |
| EP | 2 152 411 A2 | 2/2010 |
| GB | 1512625 A | 6/1978 |
| WO | WO-03/072244 A1 | 9/2003 |
| WO | WO-2004089537 A2 | 10/2004 |
| WO | WO-2006133187 A2 | 12/2006 |
| WO | WO-2007/122090 A2 | 11/2007 |
| WO | WO-2008141027 A2 | 11/2008 |
| WO | WO-2008141030 A1 | 11/2008 |
| WO | WO-2008141032 A1 | 11/2008 |
| WO | WO-2010/123856 A1 | 10/2010 |
| WO | WO-2011/109215 A1 | 9/2011 |

\* cited by examiner

CATALYST FOR THE EPOXIDATION OF ALKENES

CROSS-REFERENCE TO RELATED APPLICATIONS

This application is a national stage application (under 35 U.S.C. §371) of PCT/IB2014/066466, filed December 1, 2014, which claims benefit of European Application No. 13196259.9, filed December 9, 2013, both of which are incorporated herein by reference in their entirety.

The present invention relates to a catalyst for the epoxidation of alkenes, comprising silver, rhenium, cesium, lithium, tungsten and sulfur on a support. The present invention further relates to a process for producing the catalyst and the use of the catalyst for the oxidation of alkylenes to alkylene oxides. In addition, the present invention relates to a process for preparing ethylene oxide from ethylene, which comprises the oxidation of ethylene with oxygen in the presence of said catalyst.

BACKGROUND OF THE INVENTION

Ethylene oxide is an important basic chemical and frequently prepared on an industrial scale by direct oxidation of ethylene with oxygen in the presence of silver-containing catalysts. These catalysts usually comprise metallic silver and further elements, which have been deposited on a support material by means of a suitable process. As supports, it is in principle possible to use various porous materials such as activated carbon, titanium dioxide, zirconium dioxide or silicon dioxide or ceramic compositions or mixtures of these materials. In general, alpha-aluminum oxide is used as support.

Apart from silver as active component, these catalysts often comprise promoters for improving the catalytic properties (WO 2007/122090, WO 2010/123856). Examples of promoters are alkali metal compounds and/or alkaline earth metal compounds. Some documents teach the use of transition metals such as cobalt (EP 0 480 538), tungsten or molybdenum. A particularly preferred promoter for influencing the activity and selectivity of catalysts is rhenium (EP 0 266 015). In industry, preference is given to using catalysts comprising rhenium and/or other transition metal promoters in combination with alkali metal compounds and/or alkaline earth metal compounds because of their high selectivity. Selectivity is, for example in the case of the oxidation of ethylene, the molar percentage of ethylene which reacts to form ethylene oxide. The activity of the catalyst is usually characterized by the ethylene oxide concentration at the reactor outlet under otherwise constant conditions, for example temperature, pressure, gas throughput, amount of catalyst, etc. The higher the ethylene oxide concentration in the reactor output stream, the higher the activity of the catalyst. The lower the temperature required for achieving a predetermined ethylene oxide concentration, the higher the activity.

The direct oxidation of ethylene to ethylene oxide using supported silver catalysts is described, for example, in DE-A-2300512, DE-A 2521906, EP-A-0014457, DE-A-2454972, EP-A-0172565, EP-A-0357293, EP-A-0266015, EP-A-0011356, EP-A-0085237, DE-A-2560684 and DE-A2753359.

EP 1 613 428 B1 describes the production of ethylene oxide from ethylene using a catalyst containing rhenium in an amount of at most 1.5 mmol/kg with respect to the total weight of the catalyst or 0.0015 mmol/m$^2$ with respect to the BET surface area of the support. EP 2 152 411 A2 describes the use of promoters and co-promoters consisting of sulfur, phosphorus, boron, or mixtures thereof, tungsten, molybdenum, chromium, such that the quantity of the co-promoter deposited on the support is at most 3.8 mmol/kg relative to the weight of the support.

SUMMARY OF THE INVENTION

It was an object of the present invention to provide novel catalysts for the epoxidation of alkenes, which display advantageous activities and/or selectivities.

Accordingly, novel catalysts for the epoxidation of alkenes have been found, comprising silver, rhenium, cesium, lithium, tungsten and sulfur on a support, wherein the tungsten is deposited on the support as a tungsten compound with a very low sulfur to tungsten atomic ratio. Although sulfur is a known promoter for use in ethylene oxide catalysts, the use of low-sulfur or sulfur-free tungsten compounds during the catalyst production provides catalysts with improved catalyst activity and selectivity, even though sulfur is added separately as a promoter during the production process.

DETAILED DESCRIPTION OF THE INVENTION

One embodiment of the present invention is a catalyst for the epoxidation of alkenes, comprising silver, rhenium, cesium, lithium, tungsten and sulfur on a support, wherein the tungsten has been deposited on the support as a tungsten compound with a sulfur to tungsten atomic ratio of 150 ppm or less.

The catalyst of the invention comprises a support. Supports suitable for the purposes of the invention can be produced by processes known from the prior art. Examples are the processes described in US 2009/0198076 A1, WO 2006/133187, WO 03/072244, US 2005/0096219 A1 and EP 0 496 386 B2.

Examples of suitable support materials are aluminum oxide, silicon dioxide, silicon carbide, titanium dioxide, zirconium dioxide and mixtures thereof, with aluminum oxide being preferred. In a preferred embodiment, the present invention accordingly provides a catalyst whose support is an aluminum oxide support.

The term aluminum oxide as used here comprises all conceivable structures such as alpha-, gamma- or theta-aluminum oxide. In a preferred embodiment, the support is an alpha-aluminum oxide support. The present invention accordingly also provides a catalyst in which the support is an alpha-aluminum oxide.

In a further preferred embodiment, the alpha-aluminum oxide has a purity of at least 75% by weight, preferably a purity of at least 80% by weight, more preferably a purity of at least 85% by weight, more preferably a purity of at least 90% by weight, more preferably a purity of at least 98% by weight, more preferably a purity of at least 98.5% by weight and particularly preferably a purity of at least 99% by weight.

The term alpha-aluminum oxide accordingly also comprises alpha-aluminum oxides which comprise further constituents, for example elements selected from the group consisting of zirconium, alkali metals, alkaline earth metals, silicon, zinc, gallium, hafnium, boron, fluorine, copper, nickel, manganese, iron, cerium, titanium, chromium and compounds of these elements and also mixtures of two or more of these elements and/or compounds thereof.

In general, a catalyst support suitable for the purposes of the present invention can be produced by mixing an aluminum oxide, aluminum hydroxide, aluminum oxide hydroxide, aluminum alkoxylate and/or mixture thereof with water and optionally with an organic solvent and also a burnout material or a pore former and at least one binder. Suitable pore formers are organic solid materials with a certain particle size distribution which determines the size of the cavities in the support which are left after the organic material has been transformed into gaseous products during the calcination step. Typical examples are cellulose and cellulose derivatives such as methylcellulose, ethylcellulose, carboxymethylcellulose or polyolefins such as polyethylene and polypropylene or natural burnout materials such as ground walnut shells. The pore formers are selected so that they are completely burnt out of the aluminum oxide to form the finished alpha-aluminum oxide support at the furnace temperatures selected for the calcination. Suitable binders or extrusion aids are described, for example, in EP 0 496 386 B2. Mention may be made by way of example of aluminum oxide gels with nitric acid or acetic acid, cellulose, e.g. methylcellulose, ethylcellulose or carboxyethylcellulose or methyl stearate or ethyl stearate, polyolefin oxides, waxes and similar substances.

The paste formed by mixing can be brought to the desired shape by extrusion. To assist the extrusion process, it is possible to use extrusion aids.

The shaped body obtained as described above is, after shaping, usually optionally dried and calcined to give the aluminum oxide support. Calcination is usually carried out at temperatures in the range from 1200° C. to 1600° C. It is usual to wash the aluminum oxide support after calcination in order to remove soluble constituents.

The alpha-aluminum oxide can comprise the further constituents in any suitable form, for example as elements and/or in the form of one or more compounds. If the alpha-aluminum oxide comprises one or more constituents in the form of a compound, it comprises these as, for example, oxide or mixed oxide. Supports which are suitable for the purposes of the invention therefore also include alpha-aluminum oxides comprising at least one further constituent selected from the group consisting of silicon dioxide, sodium oxide, potassium oxide, calcium oxide and magnesium oxide, nickel oxide, gallium oxide, hafnium oxide, copper oxide, iron oxide and mixtures thereof.

As regards the amount of the further constituents, the totality of the further constituents is preferably in the range of less than 25% by weight, more preferably less than 20% by weight, more preferably less than 15% by weight, more preferably less than 10% by weight, more preferably less than 5% by weight, more preferably less than 2% by weight, more preferably less than 1.5% by weight and particularly preferably less than 1% by weight, based on the total weight of the support.

If the support comprises, for example, alkali metals, it preferably comprises these in a total amount in the range from 10 to 2500 ppm, more preferably in an amount of from 10 to 1000 ppm, more preferably in an amount of from 50 to 850 ppm, based on the total weight of the support and calculated as element. In an embodiment, the support comprises at least one alkali metal selected from the group consisting of sodium and potassium. If the support comprises, for example, sodium, it preferably comprises this in an amount in the range from 10 to 1500 ppm, more preferably in an amount of from 10 to 800 ppm, more preferably in an amount of from 10 to 500 ppm, based on the total weight of the support and calculated as element. If the support comprises, for example, potassium, it preferably comprises this in an amount in the range from 10 to 1000 ppm, more preferably in an amount of from 10 to 500 ppm, more preferably in an amount of from 10 to 300 ppm, based on the total weight of the support and calculated as element. In an embodiment of the invention, the support comprises, for example, sodium in an amount of from 10 to 1500 ppm and potassium in an amount of from 10 to 1000 ppm.

The present invention accordingly also describes a catalyst whose support comprises sodium in an amount of from 10 to 1500 ppm and potassium in an amount of from 10 to 1000 ppm, particularly preferably sodium in an amount of from 10 to 500 ppm and potassium in an amount of from 10 to 300 ppm, based on the total weight of the support and in each case calculated as element.

If the support comprises, for example, alkaline earth metals, it preferably comprises these in a total amount in the range of up to 2500 ppm, for example in the range from 10 to 2500 ppm, more preferably in an amount of from 10 to 1200 ppm, more preferably in an amount of from 10 to 700 ppm, based on the total weight of the support and calculated as element. In an embodiment, the support comprises at least one alkaline earth metal selected from the group consisting of calcium and magnesium. If the support comprises, for example, calcium, it preferably comprises this in an amount in the range from 10 to 1500 ppm, more preferably in an amount of from 10 to 1000 ppm, more preferably in an amount of from 10 to 500 ppm, based on the total weight of the support and calculated as element. If the support comprises, for example, magnesium, it preferably comprises this in an amount in the range from 10 to 800 ppm, more preferably in an amount of from 10 to 500 ppm, more preferably in an amount of from 10 to 250 ppm, based on the total weight of the support and calculated as element.

The present invention accordingly also describes a catalyst whose support comprises magnesium in an amount of from 10 to 800 ppm and calcium in an amount of from 10 to 1500 ppm, in each case based on the total weight of the support and calculated as element. The support particularly preferably comprises, for example, sodium in an amount of from 10 to 1500 ppm, potassium in an amount of from 10 to 1000 ppm, magnesium in an amount of from 10 to 800 ppm, and calcium in an amount of from 10 to 1500 ppm, in each case based on the total weight of the support and calculated as element.

If the support comprises, for example, silicon, it preferably comprises this in an amount in the range from 50 to 10000 ppm, more preferably in an amount of from 50 to 5000 ppm, more preferably in an amount of from 50 to 600 ppm, based on the total weight of the support and calculated as element.

A support which is preferred for the purposes of the present invention is, for example, an alpha-aluminum oxide which has a purity of at least 90% and comprises from 50 to 10000 ppm of silicon, from 10 to 1500 ppm of sodium and from 10 to 2500 ppm of alkaline earth metals in total, in each case calculated as element and based on the total weight of the support. The support preferably comprises calcium and/or magnesium as alkaline earth metal. Particular preference is given to an alpha-aluminum oxide which has a purity of at least 98% by weight and comprises from 50 to 5000 ppm of silicon, from 10 to 800 ppm of sodium and from 10 to 700 ppm of alkaline earth metals in total, in each case calculated as element and based on the total weight of the support.

The support used for the catalyst of the invention preferably has a BET surface area, determined in accordance with the method described in the standard ISO 9277, of from 0.1 to 5 m²/g, more preferably in the range from 0.1 to 2 m²/g, more preferably in the range from 0.5 to 1.5 m²/g, more preferably in the range from 0.6 to 1.3 m²/g and particularly preferably in the range from 0.6 to 1.0 m²/g.

Furthermore, the supports used for the catalyst of the invention preferably have pores having diameters in the range from 0.1 to 100 μm, with the pore size distribution being able to be monomodal or polymodal, for example bimodal, trimodal or tetramodal. The supports preferably have a bimodal pore size distribution. The supports more preferably have a bimodal pore size distribution having peak maxima in the range from 0.1 to 10 μm and from 15 to 100 μm, preferably in the range from 0.1 to 5 μm and from 17 to 80 μm, more preferably in the range from 0.1 to 3 μm and from 20 to 50 μm, more preferably in the range from 0.1 to 1.5 μm and from 20 to 40 μm. The pore diameters are determined by Hg porosimetry (as described in the standard DIN 66133:1993-06). The term "bimodal pore size distribution having peak maxima in the range from 0.1 to 10 μm and from 15 to 100 μm", as used above, indicates that one of the two peak maxima is in the range from 0.1 to 10 μm and the other peak maximum is in the range from 15 to 100 μm.

The present invention accordingly also describes a catalyst whose support has a bimodal pore size distribution, preferably a bimodal pore size distribution comprising at least pores having a pore diameter in the range from 0.1 to 15 μm and pores having a pore diameter in the range from 15 to 100 μm, determined by Hg porosimetry.

The geometric shape of the support is generally of minor importance, but the support should advantageously be in the form of particles which allow unhindered diffusion of the reaction gases to a very large part of the outer surface area coated with the catalytically active silver particles and optionally further promoters and internal surface area of the support. The selected geometric shape of the support should ensure a very small pressure drop over the entire reactor length. In a preferred embodiment, the support is used as shaped bodies, for example as extrudate, hollow extrudate, star extrudate, sphere, ring or hollow ring. The support is preferably a shaped body having the geometry of a hollow body. Particular preference is given to cylinders having the following geometries (external diameter×length×internal diameter, in each case reported in mm): 5×5×2, 6×6×3, 7×7×3, 8×8×3, 8×8.5×3, 8×8.5×3.5, 8.5×8×3.5, 8.5×8×3, 9×9×3, 9.5×9×3, 9.5×9×3.5. Each length indicated is subject to tolerances in the region of ±0.5 mm.

According to the invention, it is also possible for the catalyst to be used in the form of crushed catalyst material obtained from one or more of the shaped bodies mentioned.

The water absorption of the support is, for example, in the range from 0.35 ml/g to 0.65 ml/g, preferably in the range from 0.42 ml/g to 0.52 ml/g, determined by vacuum cold-water uptake.

The catalyst of the invention comprises silver as active metal. The catalyst can comprise silver in an amount of, for example, from 5 to 35% by weight, in particular from 10 to 30% by weight, preferably in an amount of from 10 to 25% by weight, based on the total weight of the catalyst and calculated as element. The silver is preferably deposited on the support in the form of a silver compound, which can be a salt or a silver complex. The silver compound is preferably applied as a solution, in particular as a solution in water. In order to obtain the silver compound in soluble form, a complexing agent such as ethanolamine, EDTA, 1,3- or 1,2-propanediamine, ethylenediamine and/or an alkali metal oxalate can also be added in an appropriate way to the silver compound, for example silver (I) oxide or silver (I) oxalate and this complexing agent can also simultaneously act as reducing agent. Silver is particularly preferably applied in the form of a silver-amine compound, particularly preferably a silver-ethylenediamine compound.

Furthermore, the catalyst of the invention comprises one or more further elements as promoters. For the purposes of the present invention, a promoter is a constituent of the catalyst by means of which an improvement in one or more catalytic properties, e.g. selectivity, activity, conversion, yield and/or operating life, compared to a catalyst which does not comprise the constituent is achieved. Preference is given to compounds which under the reaction conditions are chemically stable and do not catalyze any undesirable reactions. Promoters are usually used in a total amount of from 10 to 3000 ppm and each in an amount of from 5 to 1500 ppm, more preferably each in an amount of from 10 to 1300 ppm and particularly preferably each in an amount of from 50 to 1300 ppm, based on the total weight of the catalyst and calculated as sum of the elements. Promoters are preferably applied in the form of compounds to the support, for example in the form of complexes or in the form of salts, for example in the form of halides, fluorides, bromides or chlorides, or in the form of carboxylates, nitrates, sulfates or sulfides, phosphates, cyanides, hydroxides, carbonates, oxides, oxalates or as salts of heteropolyacids, for example in the form of salts of heteropolyacids of rhenium.

The catalyst of the invention comprises rhenium as a promoter. The catalyst can comprise rhenium in an amount of from 50 to 600 ppm, more preferably in an amount of from 100 to 450 ppm, more preferably in an amount of from 150 to 400 ppm, based on the total weight of the catalyst and calculated as element. Rhenium is preferably applied as a compound, for example as halide, oxyhalide, oxide, rhenate, perrhenate or as acid. Examples of suitable rhenium compounds are ammonium perrhenate, rhenium(III) chloride, rhenium(V) chloride, rhenium(V) fluoride, rhenium(VI) oxide and rhenium(VII) oxide. For the purposes of the invention, rhenium is particularly preferably applied as ammonium perrhenate to the support.

The catalyst of the invention comprises cesium as a promoter. The catalyst can comprise cesium in an amount of from 20 to 850 ppm, in particular in an amount of from 100 to 600 ppm, based on the total weight of the catalyst and calculated as element. Cesium is preferably applied as cesium compound to the support. Here, any suitable cesium compound can in principle be used. Cesium is preferably applied in the form of cesium hydroxide.

The catalyst of the invention comprises lithium as a promoter. The catalyst can comprise lithium in an amount of from 10 to 450 ppm, in particular in an amount of from 50 to 300 ppm, based on the total weight of the catalyst and calculated as element. Lithium is preferably applied as lithium compound to the support. Here, any suitable lithium compound can in principle be used. Lithium is preferably applied in the form of lithium nitrate.

The catalyst of the invention comprises sulphur as a promoter. The catalyst can comprise sulfur in an amount of from 5 to 300 ppm, in particular in an amount of from 5 to 150 ppm, based on the total weight of the catalyst and calculated as element. Sulfur is preferably applied as sulfur compound to the support. Here, any suitable sulfur compound can in principle be used. Sulfur is preferably applied in the form of ammonium sulfate.

The catalyst of the invention comprises tungsten as a promoter. In nature, tungsten is found almost exclusively in the form of tungstates, including wolframite (a solid mixture of isomorphous $FeWO_4$ and $MnWO_4$), scheelite ($CaWO_4$), and stolzite ($PbWO_4$). Tungsten ores are concentrated by mechanical and magnetic processes and the concentrates attacked by fusion with NaOH. The cooled melts are leached with water, which gives a sodium tungstate solution from which hydrous $WO_3$ is precipitated on acidification. $WO_3$ (anhydrous) is a yellow solid (mp. 1200° C.) and has a slightly distorted form of the cubic rhenium trioxide structure. Many tungsten oxides are known, including $WO_3$ and $WO_2$ along with other non-stoichiometric oxides. $WS_2$ and $WS_3$ compounds are commonly found in nature, although hydrated $W_2S_5$, anhydrous $W_2S_5$, and a few others including $W_2S_3$ and $WS_4$ are known. They can be prepared by direct combination of the elements, by heating $WO_3$ in $H_2S$, or by fusing $WO_3$ with sulfur and potassium carbonate. R. P. Singh Gaur (JOM 2006, Vol. 58, No. 9, pages 45 to 49) teaches that typical natural sources of tungsten (such as scheelite) contain significant amounts of sulfur (for example, up to 2.0 wt. %) and that during the process of refining the tungstic oxide from the ore, sulfur containing compounds such as NaHS are used to remove small amounts of molybdenum. Sodium impurities are removed using sulfate salts of primary or secondary amines. From this information one can conclude that the presence of sulfur in commercially available tungstic acid can be expected and that the nature of these sulfur containing compounds can be a sulfide, hydrogen sulfide, polysulfide, poly hydrogen sulfide, sulfite, sulfate and mixtures thereof. S. Prasad (Can. J. Chem. 1981, Vol. 59, pages 563 to 565) discloses that anions $(WO_4)^{2-}$ can react with $H_2S$ to form oxo-thio tungstates such as $(WO_3S)^{2-}$, $(WO_2S_2)^{2-}$ and $(WOS_3)^{2-}$ and/or thiotungstate anions $(WS_4)^{2-}$. The thiotungstate moieties can be present in the form of $WS_3$, $(WS_4)^{2-}$, $(W_2S_7)^{2-}$, $(W_4S_{13})^{2-}$ or $(W_4S_{15})^{4-}$ or mixtures thereof. This shows that sulfur in tungstic acid could also come from exposure of tungstic acid to sulfur compounds contained in the air.

The catalyst can comprise tungsten in an amount of from 10 to 600 ppm, more preferably in an amount of from 50 to 400 ppm, more preferably in an amount of from 80 to 250 ppm, based on the total weight of the catalyst and calculated as element. According to the invention tungsten has to be applied as a compound, for example as halide, hydroxide, oxalate, oxide, tungstate or as acid, that has a sulfur to tungsten atomic ratio of 150 ppm or less, preferably of 100 ppm or less, more preferably of 50 ppm or less, even more preferably of 10 ppm or less. Examples of suitable tungsten compounds are tungsten oxides like tungsten(VI) oxide, tungstic acid, sodium polytungstate, ammonium paratungstate, phosphotungstic acid and any other heteropolyacid of tungsten, which are commercially available or can be prepared by known methods. For the purposes of the invention, tungsten is particularly preferably applied as tungstic acid to the support.

In a particularly preferred embodiment, the catalyst of the invention comprises silver in an amount of from 10 to 25% by weight, rhenium in an amount of from 150 to 450 ppm, cesium in an amount of from 100 to 600 ppm, lithium in an amount of from 50 to 300 ppm, tungsten in an amount of from 80 to 250 ppm and sulfur in an amount of from 5 to 150 ppm on a support, all amounts based on the total weight of the catalyst and calculated as element, wherein the tungsten has been deposited on the support as a tungsten compound with a sulfur to tungsten atomic ratio of 150 ppm or less.

In another embodiment the catalyst of the invention comprises silver, rhenium, cesium, lithium, tungsten and sulfur as described above and also at least one further promoter, for example five, four, three or two further promoters or one further promoter. All promoters known in the prior art are conceivable as at least one further promoter. The at least one further promoter is preferably selected from the group consisting of sodium, potassium, rubidium, beryllium, magnesium, calcium, strontium, barium, manganese, molybdenum, cadmium, chromium, tin and mixtures of two or more thereof. The catalyst particularly preferably comprises at least one further promoter selected from the group consisting of chromium, manganese, molybdenum, tin and mixtures of two or more thereof.

The promoters, more preferably the promoter compounds, are preferably dissolved in a suitable solvent, preferably in water, before application. The support is then preferably impregnated with the resulting solution comprising one or more of the promoters. If a plurality of promoters are to be added, these can be applied either together or separately to the support in a single impregnation step or in a plurality of impregnation steps. As regards the solution comprising one or more of the promoters, this can be produced in any suitable way. For example, the promoters can be dissolved separately in one solution each and the resulting solutions comprising in each case one promoter can subsequently be used for the impregnation. It is likewise possible to dissolve two or more promoters together in a solution and subsequently use the resulting solution for the impregnation. In addition, it is possible to combine the resulting solutions comprising at least one promoter before impregnation and apply the resulting solution comprising all promoters to the support.

If, for example, at least tungsten, cesium, lithium, sulfur and rhenium are used as promoters, in a particularly preferred embodiment at least one solution comprising cesium, a further solution comprising tungsten, a further solution comprising lithium and sulfur, a further solution comprising rhenium are produced. The solutions are either applied to the support in separate impregnation steps or are combined to form one solution before application and only then used for impregnation. The solutions are preferably applied together, more preferably together with the mixture comprising silver as silver-amine compound, preferably as silver-ethylenediamine compound, to the support.

As regards the application of silver, this can be applied to the support by means of all impregnation and deposition processes of the prior art for producing silver catalysts for the preparation of ethylene oxide, with these processes being able to comprise one or more impregnation and calcination steps. Appropriate production processes for silver catalysts are, for example, disclosed in DE-A 23005112, DE-A 2521906, EP-A 0 014 457, EP-A 0 085 237, EP-A 0 0384 312, DE-A 2454927, DE-A 3321895, EP-A 0 229 465, DE-A 3150205, EP-A 0 172 565 and EP-A 0 357 293.

The silver can be applied separately or together with one or more promoters. Preference is given to applying a mixture comprising silver and at least one promoter to the support, for example by impregnation, spraying or mixing processes. The order of application of the promoters and of the silver can generally be chosen at will, i.e. embodiments in which silver and the promoters are applied simultaneously to the support are comprised. Likewise, embodiments in which silver and the promoters are applied in various steps to the support are comprised, with the order of the steps generally being able to be chosen at will. Furthermore, embodiments in which part of the promoters is applied to the support before or after application of the silver and the remaining part is applied simultaneously with silver are comprised. Preference is given to applying silver and the promoters simultaneously to the support.

Another embodiment of the present invention is a process for producing catalysts for the epoxidation of alkenes, which comprises the deposition of silver, rhenium, cesium, lithium, tungsten and sulfur on a support, wherein the tungsten has to be deposited on the support as a tungsten compound with a sulfur to tungsten atomic ratio of 150 ppm or less.

The application can in principle be carried out by any suitable methods, for example by impregnation of the support. The application is preferably effected by vacuum impregnation at room temperature. In vacuum impregnation, the support is preferably firstly treated at a pressure in the range of not more than 500 mbar, more preferably at a pressure of not more than 250 mbar and particularly preferably at a pressure of not more than 50 mbar, and preferably at a temperature in the range from 2° C. to 50° C., more preferably at a temperature in the range from 5° C. to 30° C. and particularly preferably at room temperature. The vacuum treatment is, for example, carried out for a time of at least 1 minute, preferably at least 5 minutes, more preferably for a time in the range from 5 minutes to 120 minutes, in particular in the range from 10 minutes to 45 minutes, particularly preferably in the range from 15 minutes to 30 minutes. After the vacuum treatment, the at least one solution, for example the mixture comprising silver, molybdenum and tin or at least one solution comprising at least one further promoter, preferably the mixture comprising silver, molybdenum and tin and the at least one further promoter, is applied to the support. The solution is preferably dripped on or sprayed on, preferably sprayed on. Application is in this case preferably effected by means of a nozzle. After the application, the support is preferably evacuated further. The evacuation is preferably carried out at a pressure in the range of not more than 500 mbar, more preferably at a pressure of not more than 250 mbar and particularly preferably at a pressure of not more than 50 mbar, and preferably at a temperature in the range of from 2° C. to 50° C., more preferably at a temperature in the range of from 5° C. to 30° C., and particularly preferably at room temperature. The vacuum treatment is carried out, for example, for a time of at least 1 minute, preferably at least 5 minutes, more preferably for a time in the range from 5 minutes to 120 minutes, in particular in the range from 10 minutes to 45 minutes, particularly preferably in the range from 10 minutes to 20 minutes.

The application of silver, rhenium, cesium, lithium, tungsten and sulfur and optionally further promoters to a support can be followed by at least one after-treatment step, for example one, two or more drying steps. Drying is usually carried out at temperatures in the range of from 2 to 200° C. The after-treatment step is drying by means of vacuum treatment, for example, as described above.

Accordingly, another embodiment of the present invention is a process for producing catalysts for the epoxidation of alkenes, which comprises the deposition of silver, rhenium, cesium, lithium, tungsten and sulfur on a support and a drying step, wherein the tungsten has to be deposited on the support as a tungsten compound with a sulfur to tungsten atomic ratio of 150 ppm or less.

The support material is preferably calcined after the application of silver, rhenium, cesium, lithium, tungsten and sulfur and optionally further promoters, optionally after a drying step. Calcination is preferably carried out at temperatures in the range of from 150 to 750° C., preferably in the range of from 200 to 500° C., more preferably in the range of from 220 to 350° C., more preferably in the range of from 250 to less than 300° C. and particularly preferably in the range of from 270 to 295° C., with the calcination time generally being at least 5 minutes or more, for example in the range of from 5 minutes to 24 hours or in the range of from 10 minutes to 12 hours. The calcination time is particularly preferably in the range of from 5 minutes to 3 hours. The calcination can be carried out at a constant temperature. Furthermore, embodiments in which the temperature is altered continuously or discontinuously during the calcination time are comprised.

The calcination can be carried out under any gas atmosphere suitable for this purpose, for example in an inert gas or a mixture of inert gas and from 10 ppm to 21% by volume of oxygen. Inert gases which may be mentioned are, for example, nitrogen, argon, carbon dioxide, helium and mixtures of the abovementioned inert gases. If the calcination is carried out in an inert gas, nitrogen is particularly preferred. In an alternative preferred embodiment, air and/or lean air are/is used.

Furthermore, the calcination is preferably carried out in a muffle furnace, convection oven, in a rotary furnace and/or a belt calcination oven.

Accordingly, another embodiment of the present invention is a process for producing catalysts for the epoxidation of alkenes, which comprises the deposition of silver, rhenium, cesium, lithium, tungsten and sulfur on a support and a drying step and a calcination, preferably at a temperature in the range of from 270 to 295° C., wherein the tungsten has to be deposited on the support as a tungsten compound with a sulfur to tungsten atomic ratio of 150 ppm or less.

In a preferred embodiment of the present invention, the support material impregnated with silver, rhenium, cesium, lithium, tungsten and sulfur obtained by the above-described process, which has a temperature $T_0$, is calcined in a multistage process. This process comprises at least the following steps:

(1) heating the impregnated support material from the temperature $T_0$ to a temperature $T_1$ at a heating rate of at least 30 K/min, preferably in the range from 30 to 150 K/min, more preferably in the range from 30 to 80 K/min, even more preferably in the range from 40 to 75 K/min;

(2) holding the support material which has been heated to the temperature $T_1$ at a temperature $T_2$, where $T_2$ is preferably in the range from $0.95\ T_1$ to $1.1\ T_1$;

(3) cooling the support material which has been held at the temperature $T_2$ to a temperature $T_3$, where $T_3$ is not more than 60° C.

Should the impregnated support material be obtained at a temperature of greater than To in the impregnation, in particular in the particularly preferred one-step impregnation, it is, according to the invention, firstly cooled to the temperature $T_0$.

Temperatures To in the range up to 35° C., for example in the range up to 30° C. are conceivable in principle. The temperature $T_0$ is preferably in the range from 5 to 20° C., more preferably in the range from 10 to 15° C.

In preferred embodiments, the temperature $T_0$ is, according to the invention, such that the impregnated support material obtained does not have to be subjected to predrying before it is heated according to the invention at a heating rate of at least 30 K/min in step (1).

The present invention thus preferably provides a process in which the support material impregnated with silver, rhenium, cesium, lithium, tungsten and sulfur and optionally further promoters obtained by the above-described process is not subjected to a temperature which is greater than 35° C., preferably greater than 30° C., more preferably greater than 25° C. and more preferably greater than 20° C., before being heated at a heating rate of at least 30 K/min.

In step (1) of the calcination process according to the invention, the impregnated support material which has been provided at the temperature $T_0$ is heated at a heating rate of at least 30 K/min.

Heating rates of up to 150 K/min, for example up to 100 K/min or 80 K/min, are conceivable. The heating rate in step (1) is preferably in the range from 30 to 150 K/min, more preferably in the range from 30 to 80 K/min, even more preferably in the range from 40 to 75 K/min.

In step (1) of the calcination process according to the invention, the support material is heated from the temperature $T_0$ to the temperature $T_1$.

According to the invention, heating is carried out to temperatures $T_1$ which are suitable for calcination of the impregnated support material. Here, temperatures $T_1$ of up to 350° C., for example up to 340° C. or up to 330° C. or up to 320° C. or up to 310° C. or up to 300° C., are conceivable in principle. Preferred minimum temperatures $T_1$ are in the region of 250° C. Accordingly, temperatures $T_1$ in the range from 250 to 310° C. or in the range from 250 to 300° C. are conceivable. However, it has been found, according to the invention, that it is possible to set calcination temperatures of less than 300° C. The present invention therefore provides the process as described above in which the temperature $T_1$ is less than 300° C., preferably less than or equal to 299° C.

According to the invention, the temperature $T_1$ is preferably in the range from 250 to 295° C., more preferably in the range from 260 to 295° C., more preferably in the range from 270 to 295° C., more preferably in the range from 270 to 290° C., for example in the range from 270 to 285° C., from 275 to 290° C., or from 275 to 285° C.

As concerns the way in which the heating rate according to the invention is achieved, there are in principle no restrictions. Preference is given to the support material present at the temperature To being brought into contact with a gas during heating, with further preference being given to heating the support material by means of this gas and the gas thus having a temperature which allows the support material to be heated to the temperature $T_1$.

As regards the chemical composition of the gas which is brought into contact with the support material in order to heat the support material, there are in principle no restrictions. It is thus conceivable for the gas to comprise oxygen, with mention being able to be made by way of example of oxygen contents of the gas of up to 100% by volume or up to 25% by volume. The use of air, for example, is also conceivable. Lower contents of oxygen are also conceivable, with, for example, mixtures of nitrogen and air, e.g. lean air, being conceivable. Mention may be made of oxygen contents of the gas of up to 20% by volume or up to 15% by volume or up to 10% by volume or up to 5% by volume or up to 1% by volume. For the purposes of the present invention, particular preference is given to using an inert gas or a mixture of two or more inert gases, with the oxygen content preferably being less than 10 ppm, more preferably in the range from 5 to 9 ppm, as gas for heating. As inert gases, mention may be made by way of example of nitrogen, carbon dioxide, argon and/or helium. For the purposes of the present invention, nitrogen is particularly preferably used as inert gas.

The present invention accordingly provides the process as described above in which heating in step (1) is carried out by bringing the support material into contact with an inert gas $I_1$.

The present invention preferably provides the process as described above in which heating in step (1) is carried out by bringing the support material into contact with an inert gas $I_1$ which comprises less than 10 ppm, preferably from 5 to 9 ppm, of oxygen.

The present invention more preferably provides the process as described above in which heating in step (1) is carried out by bringing the support material into contact with an inert gas $I_1$, where the inert gas is nitrogen and the inert gas comprises less than 10 ppm, preferably from 5 to 9 ppm, of oxygen.

The expression "inert gas $I_1$ comprising less than 10 ppm, preferably from 5 to 9 ppm, of oxygen" refers here to a gas mixture comprising the inert gas $I_1$ and oxygen, where the oxygen content of less than 10 ppm or from 5 to 9 ppm relates to the oxygen content of the gas mixture and the inert gas $I_1$ can be a mixture of 2 or more inert gases.

For the purposes of the present invention, the gas which is brought into contact with the support material during heating in step (1) is very particularly preferably technical-grade nitrogen, preferably obtained from fractionation of air, which typically comprises nitrogen in an amount of from 99.995 to 99.9999, oxygen in an amount of from 6 to 8 ppm and traces of noble gases.

The temperature of the gas which is brought into contact with the support material during heating is in principle selected so that the heating rates according to the invention can be made possible and the support material can be brought to the temperature $T_1$. The gas with which the support material is brought into contact during heating in step (1) preferably has a temperature in the range from $T_1$ to $1.1 T_1$, more preferably in the range from $T_1$ to $1.07 T_1$, more preferably in the range from $T_1$ to $1.05 T_1$.

The contacting of the support material with the gas in step (1) can in principle be carried out in any desired way as long as it is ensured that the heating rate according to the invention is achieved for the support material. In this regard, particular preference is given to bringing the support material into contact with a stream of the gas, preferably a stream of the inert gas $I_1$, i.e. passing the gas through the support material. Here, the volume flow of the gas is basically selected so that the heating rate according to the invention is achieved. In particular, the volume flow of the gas is selected so that the heating rate according to the invention is achieved by the combination of the temperature and the volume flow of the gas which is brought into contact with the support material. The volume flow is particularly preferably in the range from 2500 to 5000 m³/h, in particular in the range from 3200 to 4500 m³/h.

In a preferred embodiment, the present invention provides the process as described above in which an inert gas $I_1$, preferably nitrogen, is passed through the support material to be heated up in step (1), where $I_1$ preferably comprises less than 10 ppm, more preferably from 5 to 9 ppm, of oxygen, $I_1$ preferably has a temperature in the range from $T_1$ to $1.1 T_1$ and $I_1$ preferably flows through the support material at a volume flow in the range from 2500 to 5000 m³/h, more preferably from 3200 to 4500 m³/h.

During heating of the support material as per step (1), the heating rate can be constant or can vary, as long as it is ensured that the overall heating rate calculated from the temperature difference $(T_1-T_0)$ divided by the total time required for heating is at least 30 K/min, preferably in the range from 30 to 80 K/min, more preferably in the range from 30 to 75 K/min, more preferably in the range from 30 to 70 K/min. The heating rate during the total heating operation is preferably at least 30 K/min, more preferably in the range from 30 to 80 K/min, more preferably in the range from 30 to 75 K/min, more preferably in the range from 30 to 70 K/min.

Ranges which are possible according to the invention for the heating rate are, for example, from 35 to 80 K/min or from 40 to 75 K/min or from 40 to 70 K/min or from 45 to 70 K/min or from 50 to 70 K/min or from 55 to 70 K/min or from 60 to 70 K/min or from 65 to 70 K/min.

In step (2) of the calcination process according to the invention, the support material which has been heated to the temperature $T_1$ is, after heating, preferably directly after heating, maintained at a temperature $T_2$ which is suitable for the purposes of the calcination according to the invention. Preference is here given to temperatures $T_2$ in the region of the temperature $T_1$. Particular preference is given to temperatures $T_2$ in the range from 0.95 to 1.1 $T_1$, for example in the range from 0.95 to 1.05 $T_1$, from 0.96 to 1.04 $T_1$, from 0.97 to 1.03 $T_1$, from 0.98 to 1.02 $T_1$ or from 0.99 to 1.01 $T_1$. The temperature $T_2$ is preferably selected so as to be less than 300° C., preferably less than or equal to 299° C.

Holding of the support material at the temperature $T_2$ also comprises embodiments in which the value of $T_2$ is not constant during the hold time but instead varies within the above-described limits. The present invention thus also comprises, inter alia, embodiments in which the holding is carried out at two or more different temperatures which are within the above-described limits $T_2$.

The time for which the support material is held at the temperature $T_2$ is in principle not subject to any restrictions. For the purposes of the present invention, preference is given to the support being held at the temperature $T_2$ for a time in the range from 1 to 15 minutes, preferably from 2 to 10 minutes, more preferably from 3 to 5 minutes, in step (2).

As regards the way in which the holding according to the invention in step (2) is achieved, there are in principle no restrictions. During holding at the temperature $T_2$, the support material is preferably brought into contact with a gas which is at a temperature which allows the support material to be maintained at the temperature $T_2$.

As regards the chemical composition of the gas which is brought into contact with the support material in order to hold the support material at the temperature $T_2$, there are in principle no restrictions. It is thus conceivable, for instance, for the gas to comprise oxygen, with, for example, oxygen contents of the gas of up to 100% by volume or up to 25% by volume being possible. The use of air, for example, is also conceivable. Lower contents of oxygen are also conceivable, with, for example, mixtures of nitrogen and air, e.g. lean air, being conceivable. Mention may be made of oxygen contents of the gas of up to 20% by volume or up to 15% by volume or up to 10% by volume or up to 5% by volume or up to 1% by volume. For the purposes of the present invention, particular preference is given to using an inert gas or a mixture of two or more inert gases, in which the oxygen content is preferably less than 10 ppm, more preferably in the range from 5 to 9 ppm, as gas for holding at the temperature $T_2$. As inert gases, mention may be made by way of example of nitrogen, carbon dioxide, argon and helium. Particular preference is given to using nitrogen as inert gas for the purposes of the present invention.

The present invention accordingly provides the process as described above in which the holding as per step (2) is carried out by bringing the support material into contact with an inert gas $I_2$.

The present invention preferably provides the process as described above in which the holding in step (2) is carried out by bringing the support material into contact with an inert gas $I_2$ comprising less than 10 ppm, preferably from 5 to 9 ppm, of oxygen.

The present invention more preferably provides the process as described above in which the holding in step (2) is carried out by bringing the support material into contact with an inert gas $I_2$, where the inert gas is nitrogen and the inert gas comprises less than 10 ppm, preferably from 5 to 9 ppm, of oxygen.

The expression "inert gas $I_2$ comprising less than 10 ppm, preferably from 5 to 9 ppm, of oxygen" refers here to a gas mixture comprising the inert gas $I_2$ and oxygen, where the oxygen content of less than 10 ppm or from 5 to 9 ppm relates to the oxygen content of the gas mixture and the inert gas $I_2$ can be a mixture of 2 or more inert gases.

For the purposes of the present invention, the gas with which the support material is brought into contact during the holding in step (2) is very particularly preferably technical-grade nitrogen, preferably obtained from fractionation of air, which typically comprises nitrogen in amounts of from 99.995 to 99.9999% by volume, oxygen in amounts of from 6 to 8 ppm and traces of noble gases.

The temperature of the gas with which the support material is brought into contact during holding in step (2) is basically selected so that the hold temperature according to the invention can be made possible. The gas with which the support material is brought into contact during holding in step (2) preferably has a temperature in the range from $T_2$ to 1.1 $T_2$, more preferably in the range from $T_2$ to 1.07 $T_2$, more preferably in the range from $T_2$ to 1.05 $T_2$, for example in the range from $T_2$ to 1.04 $T_2$ or in the range from $T_2$ to 1.03 $T_2$ or in the range from $T_2$ to 1.02 $T_2$ or in the range from $T_2$ to 1.01 $T_2$.

The contacting of the support material with the gas in step (2) can in principle be carried out in any desired way as long as it is ensured that the holding according to the invention of the support material at the temperature $T_2$ is achieved. In this regard, particular preference is given to the support material being brought into contact with a stream of the gas, preferably with a stream of the inert gas $I_2$, i.e. the gas being passed through the support material. Here, the volume flow of the gas is basically selected so that the holding according to the invention of the support material at the temperature $T_2$ is achieved. In particular, the volume flow of the gas is selected so that the holding according to the invention of the support at the temperature $T_2$ is achieved by the combination of the temperature and the volume flow of the gas which is brought into contact with the support material. The volume flow is particularly preferably in the range from 1000 to 3000 m³/h, more preferably from 1500 to 2000 m³/h.

In a preferred embodiment, the present invention provides the process as described above in which an inert gas $I_2$, preferably nitrogen, is passed through the support material to be held at the temperature $T_2$ in step (2), where $I_2$ preferably comprises less than 10 ppm, more preferably from 5 to 9 ppm, of oxygen, $I_2$ preferably has a temperature in the range from $T_2$ to 1.05 $T_2$ and $I_2$ preferably flows through the support at a volume flow in the range from 1000 to 3000 m³/h, more preferably from 1500 to 2000 m³/h.

It is preferred, but not necessary, that the inert gas $I_1$ is used as inert gas $I_2$ for the purposes of the present invention, with, as described above, the volume flow of $I_2$ being able to be different from the volume flow of $I_1$ and/or the temperature of $I_2$ being able to be different from the temperature of $I_1$.

In step (3) of the calcination process according to the invention, the support material which has been held at the temperature $T_2$ is cooled after holding, preferably directly after holding, to a temperature $T_3$. As regards the value of $T_3$, there are in principle no particular restrictions. For the purposes of the present invention, temperatures $T_3$ of not more than 60° C. are preferred.

As regards the way in which the cooling according to the invention in step (3) is achieved, there are in principle no restrictions. During cooling to the temperature $T_3$, the support material is preferably brought into contact with a gas which has a temperature which allows the support material to be cooled to the temperature $T_3$.

As regards the chemical composition of the gas which is brought into contact with the support material in order to cool the support material to the temperature $T_3$, there are in principle no restrictions. It is thus conceivable, for instance, for an inert gas as is used, for example, in steps (1) or (2) to be used as gas. For the purposes of the present invention, particular preference is given to using a gas having an oxygen content of at least 5% by volume, preferably at least 10% by volume, more preferably at least 15% by volume, more preferably at least 20% by volume, as gas for cooling to the temperature $T_3$. In particular, air is used according to the invention for effecting cooling in step (3).

In the process of the invention, the support material is preferably cooled at a cooling rate in the range from 30 to 80 K/min, preferably in the range from 40 to 60 K/min, more preferably in the range from 45 to 55 K/min, in step (3).

The calcined and cooled support material obtained in this way can either be used as catalyst immediately after step (3) or it can be stored in a suitable way.

As regards the apparatus used for the above-described calcination process, there are essentially no restrictions as long as it is ensured that the heating according to the invention in step (1), preferably also the holding according to the invention in step (2), preferably also the cooling according to the invention in step (3) can be carried out as described above. According to the invention, preference is given to embodiments in which at least the heating in step (1), preferably the heating in step (1) and holding in step (2) and also the cooling in step (3), is/are carried out continuously. With particular preference the process of the invention is carried out in a belt calciner in respect of step (1), preferably at least in respect of steps (1) and (2).

As regards the time at which the promoters are applied, they can also be applied after the above-described calcination. As well, it is possible to apply the promoters together with the silver compound to the support.

Accordingly, the invention comprises embodiments in which the at least one further promoter, that is to say, for example, five different further promoters, four different further promoters, three different further promoters, two different further promoters or one further promoter are applied to the support and the support which has been treated in this way is only subsequently calcined as described above to give a catalyst according to the invention.

The present invention further provides a process for preparing ethylene oxide from ethylene, which comprises oxidation of ethylene in the presence of a catalyst for the epoxidation of alkenes, comprising silver, rhenium, cesium, lithium, tungsten and sulfur on a support, wherein the tungsten has been deposited on the support as a tungsten compound with a sulfur to tungsten atomic ratio of 150 ppm or less.

In addition, the present invention also provides for the use of a catalyst for the epoxidation of alkenes, comprising silver, rhenium, cesium, lithium, tungsten and sulfur on a support, wherein the tungsten has been deposited on the support as a tungsten compound with a sulfur to tungsten atomic ratio of 150 ppm or less.

According to the invention, the epoxidation can be carried out by all processes known to those skilled in the art. Here, it is possible to use all reactors which can be used in the ethylene oxide production processes of the prior art, for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987), or reactors having a loose catalyst bed and cooling tubes, for example the reactors described in DE-A 3414717, EP 0082609 and EP-A 0339748. The epoxidation is preferably carried out in at least one tube reactor, preferably in a shell-and-tube reactor. The catalyst of the invention can be used either alone or together with other catalysts in a combined or structured catalyst bed.

The preparation of ethylene oxide from ethylene and oxygen can, according to the invention, be carried out under conventional reaction conditions as are described, for example, in DE 25 21 906 A1, EP 0 014 457 A2, DE 2 300 512 A1, EP 0 172 565 A2, DE 24 54 972 A1, EP 0 357 293 A1, EP 0 266 015 A1, EP 0 085 237 A1, EP 0 082 609 A1 and EP 0 339 748 A2. Inert gases such as nitrogen or gases such as water vapour and methane which are inert under the reaction conditions and optionally reaction moderators, for example hydrocarbons or organohalides such as ethyl chloride, vinyl chloride or 1,2-dichloroethane, can additionally be mixed into the reaction gas comprising ethylene and molecular oxygen. The oxygen content of the reaction gas is advantageously in a range in which no explosive gas mixtures are present. A suitable composition of the reaction gas for preparing ethylene oxide can comprise, for example, an amount of ethylene in the range from 10 to 80% by volume, preferably from 20 to 60% by volume, more preferably from 25 to 50% by volume and particularly preferably in the range from 30 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7% by volume, based on the total volume of the reaction gas.

The reaction gas preferably comprises a chlorine-comprising reaction moderator such as ethyl chloride, methyl chloride, vinyl chloride or dichloroethane or mixtures thereof in an amount of from 0.01 to 100 ppm, preferably in an amount of from 0.1 to 25 ppm. The remainder of the reaction gas generally comprises hydrocarbons such as methane or other inert gases such as nitrogen. In addition, the reaction gas can also comprise other materials such as water vapor, carbon dioxide or noble gases.

The above-described constituents of the reaction mixture can optionally comprise small amounts of impurities. Ethylene can, for example, be used in any purity which is suitable for the epoxidation according to the invention. Suitable purities include, but are not limited to, polymer-grade ethylene, which typically has a purity of at least 99%, and chemical-grade ethylene, which has a lower purity of typically below 95%. The impurities typically comprise mainly ethane, propane and/or propene.

The epoxidation is usually carried out at elevated temperature. Preference is given to temperatures in the range from 150 to 350° C., more preferably in the range from 180 to 300° C., more preferably in the range from 190 to 280° C. and particularly preferably in the range from 200 to 280° C. The present invention accordingly also provides a process as described above in which the oxidation takes place at a temperature in the range from 180 to 300° C., preferably in the range from 200 to 280° C.

The oxidation is preferably carried out at pressures in the range from 5 bar to 30 bar. The oxidation is more preferably carried out at a pressure in the range from 5 bar to 25 bar, preferably at a pressure in the range from 10 bar to 20 bar and in particular in the range from 14 bar to 20 bar. The present invention accordingly also provides a process as described above in which the oxidation is carried out at a pressure in the range from 14 bar to 20 bar.

The oxidation is preferably carried out in a continuous process. If the reaction is carried out continuously, use is made of a GHSV (gas hourly space velocity) which is, as a function of the type of reactor selected, for example of the size/cross-sectional area of the reactor, the shape and size of the catalyst, preferably in the range from 800 to 10000/h, preferably in the range from 2000 to 6000/h, more preferably in the range from 2500 to 5000/h, where the figures are based on the volume of the catalyst.

The preparation of ethylene oxide from ethylene and oxygen can advantageously be carried out in a circulation process. Here, the reaction mixture is circulated through the reactor with the newly formed ethylene oxide and the by-products formed in the reaction being removed from the product gas stream after each pass and the product stream being, after being supplemented with the required amounts of ethylene, oxygen and reaction moderators, fed into the reactor again. The separation of the ethylene oxide from the product gas stream and its work-up can be carried out by the conventional methods of the prior art (cf. Ullmann's Encyclopedia of Industrial Chemistry, 5th edition, vol. A-10, pages 117 to 135, 123 to 125, VCH-Verlagsgesellschaft, Weinheim 1987).

The present invention is illustrated below with the aid of examples.

EXAMPLES

1. General Method for Producing Catalysts According to the Invention 1.1 Aluminum Oxide Support Used Bimodal alpha-aluminum oxide supports with a ring-geometry and properties as summarized in the following Table 1 were used for all examples. Except for an atomic ratio, "ppm" shall mean ppm by weight throughout the specification of this invention.

TABLE 1

| Support material characteristics | |
|---|---|
| Ring geometry (mm) | 8.0 × 8.5 × 2.35 |
| BET (m²/g) | 0.8 |
| Water uptake (ml/g) | 0.45 |
| Hg-Porosimetry: 2 Peak-Maxima (μm) | 1; 60 |
| Ca (ppm) | <600 |
| Fe (ppm) | <250 |
| K (ppm) | <400 |
| Mg (ppm) | <200 |
| Na (ppm) | <600 |
| Si (ppm) | <900 |
| Ti (ppm) | <100 |
| Zn (ppm) | <100 |
| Zr (ppm) | <100 |

1.1. Production of the Silver Complexation Solution 550 g of silver nitrate were completely dissolved in 1.5 L of water under constant stirring and the solution was warmed to 40° C. 402 g of KOH (47.8%) was mixed with 1.29 L water. A separate solution of 216.3 g of oxalic acid was added to the KOH solution, which was then warmed to 40° C. The potassium oxalate solution was then added to the silver nitrate solution within 45 min (volume flow rate ca. 33 mL/min) with the aid of a dosing pump and the solution was stirred for approximately 1 h at 40° C. The precipitated silver oxalate was then filtered and the obtained filter cake was washed with 1 L water portions until the filter cake was free of potassium and nitrate (ca. 10 L total). The water was removed from the filter cake by flowing air through the filter apparatus and the water content of the filter cake was measured. Typically a cake of 620 g with a water content of 20.8% was obtained.

Ethylenediamine (306 g) was cooled in an ice bath to ca. 10° C. and 245 g water was added in small portions. At the end of the water addition, 484.7 g of the (still damp) silver oxalate was added to the ethylenediamine/water mixture within 30 minutes. The mixture was stirred at room temperature overnight and any undissolved material removed via centrifugation. The silver content was determined refractometrically and the density was measured.

The obtained solution contained 29.35 weight % silver and had a density of 1.536 g/mL.

1.2. Production of the Silver and Promoter Solution

To 188.67 g of the silver complexation solution according to step 1.1. were added 1.37 g of a solution made from dissolving 28.44 g lithium nitrate (FMC, 99.3%) and 0.87 g ammonium sulfate (Merck, 99.4%) in 72.43 g water and then 2.05 g of a solution consisting of 9.40 g cesium hydroxide in water (HC Starck, 48%) and 2.72 g tungstic acid $H_2WO_4$ (HC Starck, 99.99% with a sulfur to tungsten (S/W) atomic ratio of either 0, 31, or 180 ppm) in 88.26 g water. Finally, 1.90 g of a solution made from dissolving 5.91 g ammonium perrhenate (Engelhard, 99.4%) in 94.01 g water were added. The combined solution was stirred for 5 minutes.

1.3. Impregnation of the Support with Silver and Promoter Solutions 173 g of the support material (according to Table 1) were placed in a rotary evaporator and under of vacuum pressure of 80 mbar evacuated for approximately 10 min.

The silver and promoter solution described in step 1.2. was added drop-wise to the support under vacuum within 15 minutes and then left to rotate additional 15 minutes. Thereafter, the impregnated support was left for 1 h at room temperature and normal pressure and every 15 minutes lightly mixed.

1.4. Calcination of the Impregnated Support

The impregnated support was calcined for 12 minutes at 290° C. under 8.3 m³/h flowing nitrogen in a calcination oven (Company HORO, Type 129 ALV-SP, Fabrication number 53270).

1.5. Epoxidation

The epoxidation reaction was conducted in a vertically-placed test reactor constructed from stainless steel with an inner-diameter of 6 mm and a length of 2.2 m. The reactor was heated using hot oil contained in a heating mantel at a specified temperature. The reactor was filled to a height of 212 mm with inert steatite balls (1.0-1.6 mm), then packed to a height of 1100 mm with split catalyst (particle size 0.5-0.9 mm) and then again packed with an additional 707 mm inert steatite balls (1.0-1.6 mm). The inlet gas was introduced to the top of the reactor.

The inlet gas consisted of 35 vol % ethylene, 7 vol % oxygen, 1 vol % $CO_2$, and ethylene chloride (EC) moderation of 2.5 ppm, with methane used as a balance. The reactions were conducted at a pressure of 15 bar and a GHSV of 4750 h$^{-1}$ at a workrate of 250 kg EO/m³$_{catalyst}$ h.

The reaction temperature was adjusted such that an ethylene oxide (EO) concentration of 2.7% was obtained in the outlet gas stream. Temperatures and selectivities have been measured after 100 h (i.e. during the start-up phase), 300 h (i.e. during the stabilization phase) and 500 h (i.e. beyond the stabilization phase) of operation. In the course of operating the reactor, the EC moderation was varied between 2.2 and 7.4 ppm to maximize catalyst performance with regard to selectivity and activity.

2. Produced Catalysts 2.1. Comparative Example 1 (not Inventive)

173 g of catalyst were prepared as described above in steps 1.1.-1.4. to form an ethylene oxide catalyst. The tungstic acid employed in step 1.2. with a S/W atomic ratio of 180 ppm.

The produced catalyst contained 15.5 wt % silver, rhenium in an amount of 380 ppm, cesium in an amount of 400 ppm, lithium in an amount of 190 ppm, tungsten in an amount of 200 ppm, and sulfur in an amount of 14 ppm.

This catalyst was tested as indicated above under pt. 1.5. in the test reactor. The results are shown in Table 2.

2.2. Example 2 (Inventive)

173 g of catalyst were prepared as described above in steps 1.1.-1.4. to form an ethylene oxide catalyst. The tungstic acid employed in step 1.2. with a S/W atomic ratio of 31 ppm.

The produced catalyst contained 15.5 wt % silver, rhenium in an amount of 380 ppm, cesium in an amount of 400 ppm, lithium in an amount of 190 ppm, tungsten in an amount of 200 ppm, and sulfur in an amount of 14 ppm.

This catalyst was tested as indicated above under pt. 1.5. in the test reactor. The results are shown in Table 2.

2.3. Example 3 (Inventive)

173 g of catalyst were prepared as described above in steps 1.1.-1.4. to form an ethylene oxide catalyst. The tungstic acid employed in step 1.2. with a S/W atomic ratio of 0 ppm.

The produced catalyst contained 15.5 wt % silver, rhenium in an amount of 380 ppm, cesium in an amount of 400 ppm, lithium in an amount of 190 ppm, tungsten in an amount of 200 ppm, and sulfur in an amount of 14 ppm.

This catalyst was tested as indicated above under pt. 1.5. in the test reactor. The results are shown in Table 2.

TABLE 2

| | Comparative Example 1 S/W 180 ppm in $H_2WO_4$ | | Example 2 S/W 31 ppm in $H_2WO_4$ | | Example 3 S/W 0 ppm in $H_2WO_4$ | |
|---|---|---|---|---|---|---|
| Time | Temperature | Selectivity | Temperature | Selectivity | Temperature | Selectivity |
| 100 h | 231.3° C. | 87.2% | 227.3° C. | 85.8% | 227.3° C. | 85.8% |
| 300 h | 243.2° C. | 89.9% | 239.2° C. | 90.1% | 239.2° C. | 90.1% |
| 500 h | 245.8° C. | 90.3% | 241.8° C. | 90.7% | 241.7° C. | 90.8% |

The results show that the catalysts of Examples 2 and 3 show a better activity (that is, lower operating temperatures) and selectivity relative to the one of Comparative Example 1. It has to be noted that all catalysts contained 14 ppm sulfur with respect to total catalyst weight and the only difference is in the sulfur content of the employed tungstic acid (see pt. 1.2. above).

The invention claimed is:

1. A catalyst for the epoxidation of alkenes, comprising
silver in an amount from 5 to 35% by weight,
rhenium in an amount from 50 to 600 ppm,
cesium in an amount from 20 to 850 ppm,
lithium in an amount from 10 to 450 ppm,
tungsten in an amount from 10 to 600 ppm, and
sulfur in an amount from 5 to 300 ppm,
and the above amounts are based on the weight of the total catalyst,
on a support, wherein the tungsten has been deposited on the support as a tungsten compound with a sulfur to tungsten atomic ratio of 100 ppm or less.

2. A catalyst according to claim 1, wherein the support is an aluminum oxide support.

3. A catalyst according to claim 1, wherein the support is an alpha-aluminum oxide with a purity of at least 85%.

4. A catalyst according to claim 1, wherein the support has a bimodal pore size distribution.

5. A catalyst according to claim 1, wherein the support has a bimodal pore size distribution comprising at least pores having a pore diameter in the range from 0.1 to 15 μm and pores having a pore diameter in the range from 15 to 100 μm.

6. A catalyst according to claim 1, wherein the support has a BET surface area in the range from 0.6 to 1.3 $m^2/g$.

7. A catalyst according to claim 1, comprising silver in an amount of from 10 to 25 % by weight, rhenium in an amount of from 150 to 450 ppm, cesium in an amount of from 100 to 600 ppm, lithium in an amount of from 50 to 300 ppm, tungsten in an amount of from 80 to 250 ppm and sulfur in an amount of from 5 to 150 ppm on a support, wherein the tungsten has been deposited on the support as a tungsten compound with a sulfur to tungsten atomic ratio of 100 ppm or less.

8. A catalyst according to claim 1, comprising at least one further promoter selected from the group consisting of sodium, potassium, rubidium, beryllium, magnesium, calcium, strontium, barium, manganese, molybdenum, cadmium, chromium, tin and mixtures of two or more thereof.

9. A process for producing catalysts for the epoxidation of alkenes, comprising depositing silver, rhenium, cesium, lithium, tungsten and sulfur on a support, wherein the tungsten has to be deposited on the support as a tungsten compound with a sulfur to tungsten atomic ratio of 100 ppm or less.

10. The process according to claim 9, further comprising a drying step.

11. The process according to claim 9, further comprising calcination at a temperature in the range of from 270 to 295° C.

12. A process for preparing ethylene oxide from ethylene, which comprises oxidating ethylene in the presence of the catalyst according to claim 1.

13. A process for the epoxidation of alkenes which comprises utilizing the catalyst according to claim 1.

14. A catalyst according to claim 1, wherein the tungsten has been deposited on the support as a tungsten compound with a sulfur to tungsten atomic ratio of 50 ppm or less.

15. The catalyst according to claim 1, wherein the tungsten has been deposited on the support as a tungsten compound with a sulfur to tungsten atomic ratio of 10 ppm or less.

16. The catalyst according to claim 1, wherein the tungsten is in an amount from 50 to 400 ppm.

17. The catalyst according to claim 1, wherein the tungsten is in an amount from 80 to 250 ppm.

18. The catalyst according to claim 1, wherein the support is aluminum oxide, silicon dioxide, silicon carbide, titanium dioxide, zirconium dioxide or mixtures thereof.

19. The catalyst according to claim 1, wherein
silver in an amount from 10 to 30 % by weight,
rhenium in an amount from 100 to 450 ppm,
cesium in an amount from 100 to 600 ppm,
lithium in an amount from 50 to 300 ppm,
tungsten in an amount from 50 to 400 ppm, and
sulfur in an amount from 5 to 150 ppm.

\* \* \* \* \*